Figure 1:
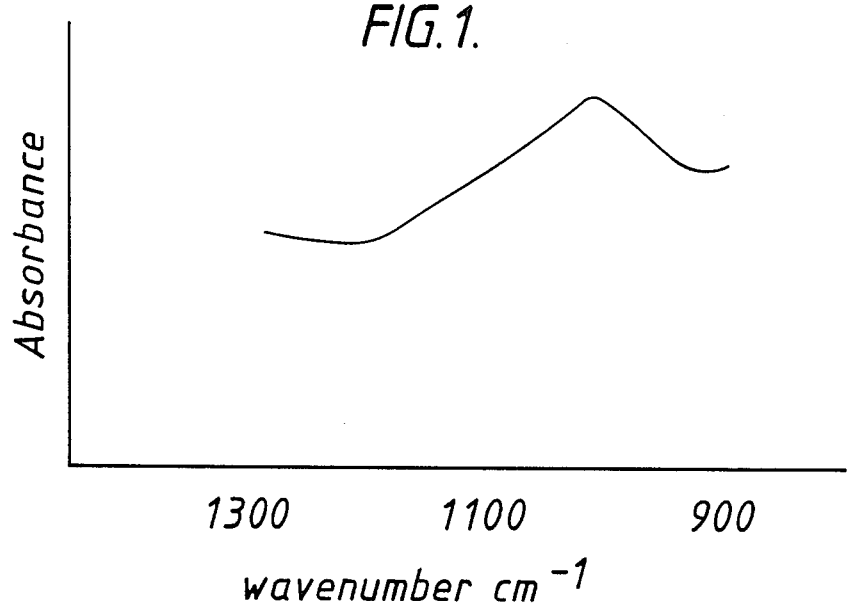

United States Patent [19]

Banks et al.

[11] Patent Number: 4,762,815

[45] Date of Patent: Aug. 9, 1988

[54] METHANATION CATALYSTS

[75] Inventors: Reginald G. S. Banks, Solihull; David R. Bates, London; Stephen D. Jones; James A. Oliver, both of Solihull, all of England

[73] Assignee: British Gas plc, London, England

[21] Appl. No.: 942,736

[22] Filed: Dec. 22, 1986

[51] Int. Cl.$^4$ .................. B01J 21/12; B01J 21/16; B01J 23/74; C07C 1/02

[52] U.S. Cl. .................. 502/259; 502/84; 502/85; 502/257; 502/258; 518/711

[58] Field of Search ............... 502/158, 259, 263, 85, 502/84, 514, 500–504, 53, 55, 257, 258

[56] References Cited

U.S. PATENT DOCUMENTS

| | | | |
|---|---|---|---|
| 2,722,504 | 11/1955 | Fleck | 502/158 |
| 3,382,189 | 5/1968 | Mitchell et al. | 502/263 |
| 3,898,182 | 8/1975 | Brown et al. | 502/263 |
| 4,046,869 | 9/1977 | Dorawala et al. | 502/55 |
| 4,253,991 | 4/1981 | Kanzler et al. | 502/259 |
| 4,323,482 | 4/1982 | Stiles et al. | 502/263 |
| 4,368,142 | 1/1983 | Frohning et al. | 502/259 |

FOREIGN PATENT DOCUMENTS

| | | | |
|---|---|---|---|
| 820257 | 9/1959 | United Kingdom . | |
| 969637 | 9/1964 | United Kingdom . | |
| 1150066 | 4/1969 | United Kingdom . | |
| 2137111 | 10/1984 | United Kingdom . | |
| 2139520 | 11/1984 | United Kingdom | 502/84 |
| 2166661 | 5/1986 | United Kingdom . | |

*Primary Examiner*—Paul E. Konopka
*Attorney, Agent, or Firm*—Staas & Halsey

[57] ABSTRACT

Silicon containing methanation catalysts e.g. those prepared by coprecipitation techniques, may be stabilized to prevent leaching of silicon species by a hydrothermal treatment comprising heating the reduced catalyst in a steam reducing gas atmosphere, lowering the temperature until liquid water species condense out, reheating to evaporate the condensed water and passivation in a mildly oxidizing atmosphere.

6 Claims, 4 Drawing Sheets

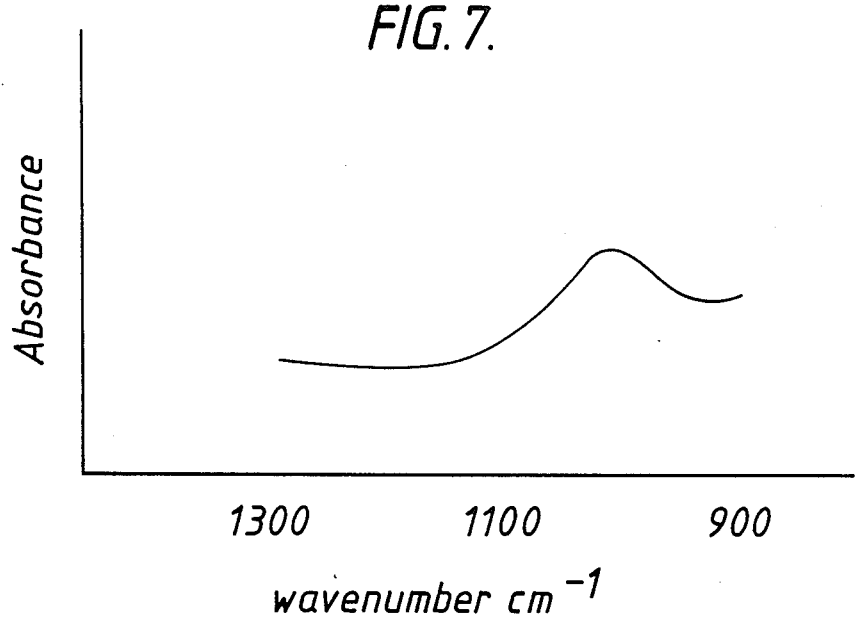

METHANATION CATALYSTS

This invention relates to catalysts, particularly methanation catalysts, to methods for their production and to the use of such catalysts.

In the production of methane-containing gases, for example by catalytically methanating synthesis gas, produced by the gasification of coal, severe reaction conditions may be encountered. Due to the high temperatures and pressures that are utilized and due to the presence of steam, conventional nickel-alumina methanation catalysts have an increasing tendency to sinter, with consequential loss of activity and mechanical strength.

Attempts to improve the mechanical strength of catalytic materials have included the use of organo-silicones as surface modifiers. For example in U.S. Pat. Nos. 2,722,504 and 4,013,590, there are disclosed techniques for impregnating metallic oxides having catalytic activity with silicones such as tetra-ethyl silicate, followed by heat treatment to decompose the organo-silicon to silica.

The mechanical strength of catalysts may also be considerably improved by the incorporation of silicates in the form of clays during the preparative stages i.e. during coprecipitation of the active catalyst materials. U.S. Pat. No. 4,546,091 and GB Patent Specification No. 2166661A describe such catalysts.

Although these catalysts have good mechanical strength and good resistance to sintering at high temperature, they do suffer from one disadvantage in use. During methanation reactions there is a tendency for silicon species to be leached out of the catalyst. Whilst this has no apparent adverse effect on the catalyst performance, deposition of the silica on downstream equipment may be deleterious and, if nothing else, has to be removed to prevent any fouling or blockages.

We have now found that silicon-containing catalyst formulations can be stabilised by post-preparative treatments.

In accordance with the present invention, there is provided a process for the preparation of catalysts suitable for methanation reactions, which includes the steps of subjecting a silicon-containing oxidic catalyst precursor to reduction in a reducing gas at a temperature greater than 450° C., thereafter contacting the thus formed catalyst mass with a mixture comprising said reducing gas and steam whilst reducing the temperature of the precursor until liquid water species are formed, and thereafter reheating the catalyst mass in the absence of oxygen until said water species have been evaporated.

If the catalyst is not to be used immediately it may be passivated by contact with a mildly oxidising atmosphere after cooling of the dried catalyst.

The process of the present invention may be applied to the known "coprecipitated" catalysts, particularly those containing nickel and aluminum, which have been modified by the incorporation of silicon or a silicon compound. Thus the process of the invention may be applied to clay-modified catalysts prepared according to our U.S. Pat. No. 4,546,091 and GB-PS-No. 2166661A. In addition the process of the invention may be applied to catalysts modified by the direct application of inorganic and/or organic silicon compounds to the catalyst precursor prior to calcination. Examples of inorganic compounds include silica in the form of colloidal silica and alkali metal silicates. Alternatively or additionally silicon modification can be effected according to the general teachings of U.S. Pat. Nos. 2,722,504 and 4,013,590.

The general procedures for preparing the precursors are described, for example, in UK-PS-Nos. 820257, 969637, 1150066, and U.S. Pat. Nos. 3,459,520, 3,511,624, 3,515,527, 3,625,665, 4,105,591 and 4,216,123.

After the production of the oxidic precursor, the catalyst is reduced according to conventional techniques. For example the oxidic precursor may be contacted with hydrogen gas at a pressure of 25 bar and at a temperature of about 500° C.

The reduced catalyst is maintained in the reducing atmosphere and may be cooled e.g. down to about 300° C. prior to introducing steam into the reducing atmosphere. For example a pure hydrogen atmosphere may be substituted with a mixture of 9 moles steam per mole hydrogen.

Within this steam/reducing gas atmosphere, the temperature of the catalyst mass is reduced until water condenses out. For example the temperature of the atmosphere, at 25 bar, may be lowered from 300° C. to about 220° C. The temperature of the catalyst is then raised after a time, typically the same time as that required for the initial reduction, e.g. 10 to 20 hours, to evaporate the water and thereafter the catalyst may be passivated.

Passivation can be effected by first replacing the steam/reducing gas atmosphere with an inert atmosphere such as nitrogen followed by cooling to ambient temperature. Thereafter the catalyst may be contacted with a mildly oxidising atmosphere for example a dilute mixture of oxygen in nitrogen, say 1% oxygen, or a carbon dioxide containing atmosphere. The passivation procedure may be that employed in our GB-PS-No. 2137111.

Determination of the presence or absence of "labile" silicon species is by analysis of the infra-red spectrum of the catalyst in the 900–1300 $cm^{-1}$ band width, which covers the region of adsorption of stretching vibrations of the Si—O bonds and Si—O—M bonds where M typically represents silicon or aluminum.

The invention will be further illustrated by the following Examples and by reference to the accompanying drawings which are plots of infra-red spectra showing absorbance against wavelength.

The infra-red spectra of the catalysts were determined by forming powdered catalyst into a disc with potassium bromide and then measuring the IR spectra on a Perkin-Elmer Spectrometer using a conventional multiple scanning technique.

EXAMPLE 1

A catalyst precursor was prepared according to the teachings of Example 4 of U.S. Pat. No. 4,105,591. 250 G of the base were placed in a flask which was then evacuated for 30 minutes. At the end of this time 90 ml (83.9 g) of tetra-ethyl silicate (TES) was run into the flask without releasing the vacuum. The flask was sealed off for 30 minutes whereupon the vacuum was released and the excess TES evaporated by heating the base in air at 100° C. for two hours. The catalyst base was then calcined in air at 450° C. for two hours to produce the oxidic precursor. po The IR-Spectra for one oxidic precursor is shown in FIG. 1. Although only one peak is shown at 1020 $cm^{-1}$, there is a clear indication of "shouldering" at about 1100 $cm^{-1}$.

A portion of the oxidic precursor was reduced with hydrogen to produce Catalyst 1A, under the conditions shown in Table 1:

TABLE 1

| Temperature | 500° C. |
|---|---|
| Pressure | 25 bar |
| Time | 16 hours |

Immediately on completion of reduction, catalyst 1A was tested in a simulated methanation test, in a feed gas consisting of 37.8% by volume steam, 36.4% by volume carbon monoxide, 18.9% by volume hydrogen, 3.8% by volume carbon dioxide and 3.1% by volume methane under the conditions given below:

| Pressure | 53 bar |
|---|---|
| Inlet temperature | 300° C. |
| Outlet temperature | 640° C. |
| Duration | 460 hours. |

Figure 2:
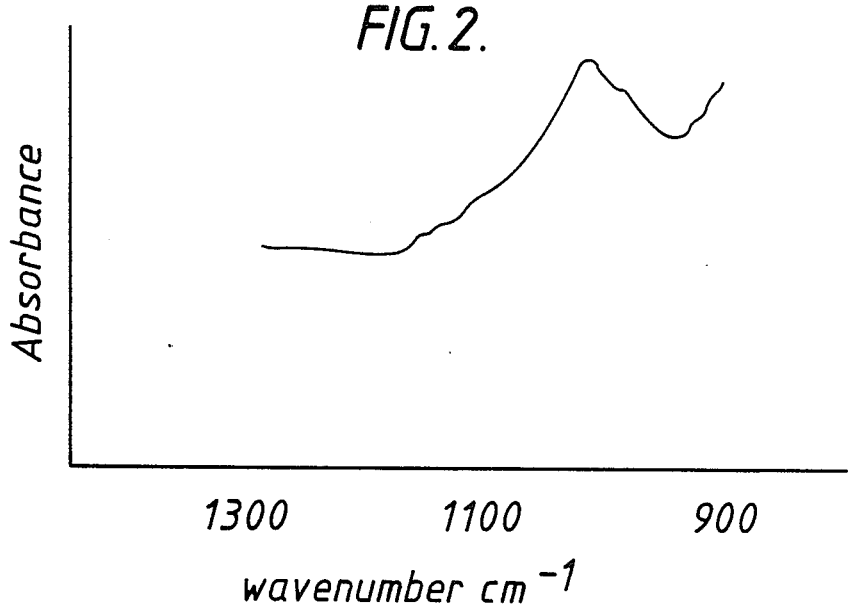

On discharge from this test the catalyst was found to have lost silica; the fresh catalyst contained about 1.7% silicon, while that discharged from the test contained only about 0.9% silicon, and indeed this silicon was found as silica deposits in the downstream pipework of the test plant. FIG. 2 shows the IR spectrum for the catalyst discharged from this test. The spectrum still shows a single predominant peak in the range 900 cm$^{-1}$ to 1100 cm$^{-1}$ at 1020 cm$^{-1}$ but it is clear that the shoulder at about 1100 cm$^{-1}$ is less apparent and so it is this silicon species that has been lost during the test.

A further sample of the oxidic precursor was reduced under the conditions described in Table 1 and then treated in accordance with the process of the invention under the following conditions to produce Catalyst 1B. The reduced catalyst was exposed to a steam/hydrogen atmosphere (9 moles steam:1 mole hydrogen) at a pressure of 25.2 bar. The temperature within the reaction chamber was reduced to 220° C., causing liquid water to condense onto the catalyst mass. The catalyst was maintained in contact with water under the above specified conditions for 16 hours after which the catalyst temperature was raised back to 300° C., and subjected to a sinter test at 550°, 25 bar for 270 hours in a 9:1 (molar) steam/hydrogen atmosphere.

Figure 3:
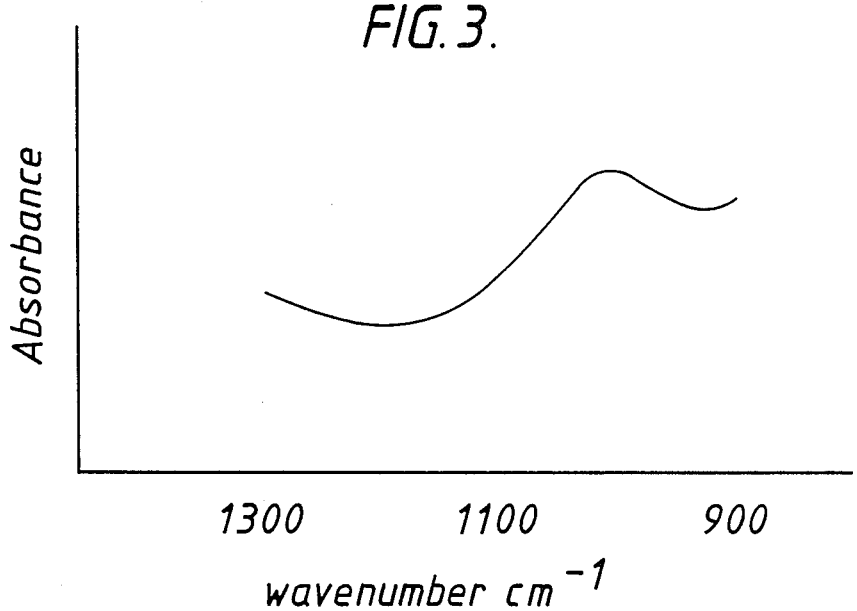

FIG. 3 is the IR Spectrum of Catalyst 1B.

This spectrum is similar to spectrum of FIG. 2 in that it has a single peak in the range 900 cm$^{-1}$ to 1100 cm$^{-1}$, in this case at around 1013 cm$^{-1}$, and does not show the shoulder associated with "labile silicon species". There was no apparent leaching of silicon species during the hydrothermal treatment of the catalyst, so the loss of the "labile silicon species" shoulder does not correspond to the leaching of silicon species from the catalyst, but instead the conversion from a labile (as indicated by its infra-red spectrum) form to a non-labile form. This was confirmed by showing that the hydrothermally treated catalyst did not lose silicon species when subject to the sinter test.

EXAMPLE 2

A catalyst was prepared and reduced according to Example 11 of GB-PS-No. 2166661 and subjected to the 270 hour steam sinter test at 550° C. as described in Example 1 herein.

Figure 4:
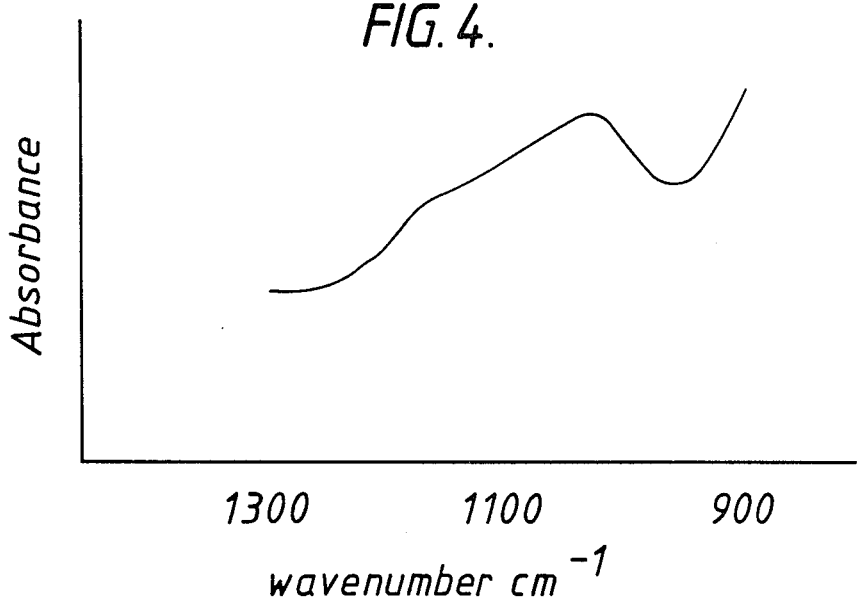
Figure 5:
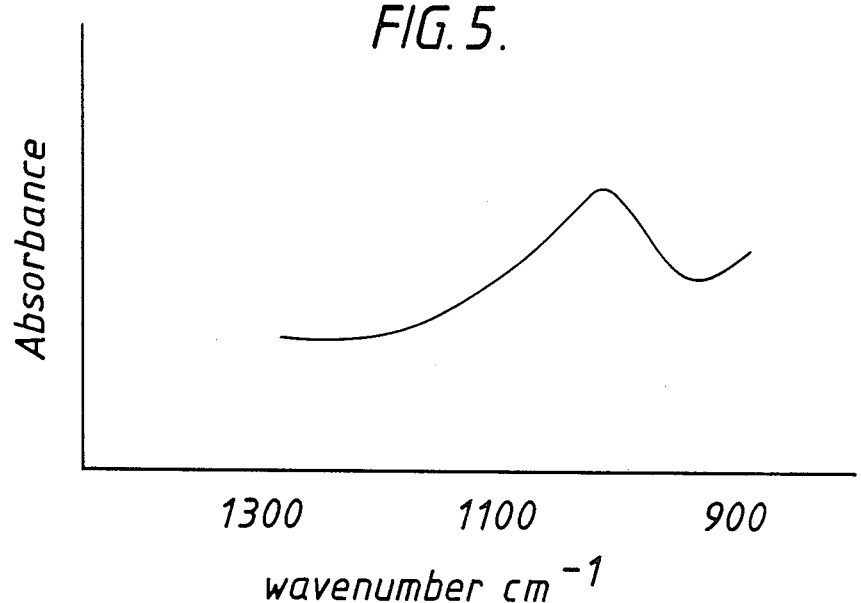

This temperature was sufficient to decompose the kaolin in the catalyst, but did not cause any leaching of silica from the catalyst. The spectrum of this catalyst (FIG. 4) again shows a single peak in the range 900 cm$^{-1}$ to 1100 cm$^{-1}$ (at 1026 cm$^{-1}$) and the shoulder at around 1100 cm$^{-1}$, associated with "labile silicon species". FIG. 5 shows the spectrum of the same catalyst but after hydrothermal treatment, as described above. Again, as can be seen from FIG. 5 there is no "labile silicon species" shoulder at around 1100 cm$^{-1}$.

EXAMPLE 3

Figure 6:
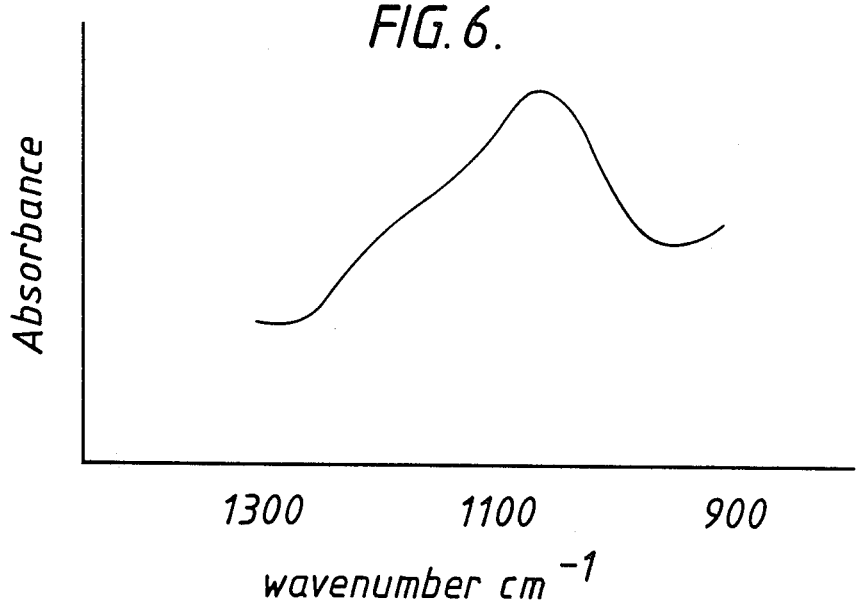

FIG. 6 is the IR Spectrum of a nickel-alumina-silica catalyst made up as follows:

A catalyst precursor was prepared from nickel nitrate (1860 g), aluminum nitrate (920 g) dissolved in 1.9 liters of water and potassium carbonate (1670 g), dissolved in 1.5 liters of water. Both solutions were heated to 90° C. and then the carbonate solution was added to the nitrate solution over a period of about 30 minutes with vigorous stirring. During the addition the temperature of the nitrate solution was maintained at 90° C. At the end of the precipitation the catalyst precursor slurry was kept stirred and at 90° C. for a further 30 munutes. The slurry was then filtered on two large Buchner filter funnels, and about 3 liters per filter of hot water sucked through, to wash out the residual potassium. The resulting cake was sucked dry and then mixed to a slurry with about 5 liters of hot water. The resulting slurry was filtered and washed on the filters as described above. This process was repeated until the potassium content of the filtrate fell below 100 p.p.m.

The procedure described above produced 2.15 kg of wet catalyst precursor cake with and overall weight loss on drying and calcination of 73%. 933 g of the wet catalyst cake (equivalent to 250 g of calcined catalyst) were blended with 52 g of Syton X30FS colloidal silica and sufficient water, about 250 ml, to form a smooth paste (Syton is a trade mark of the Monsanto Corp). The resulting paste was dried in a steam of air at 125° C., and the resulting dried catalyst precursor calcined for 2 hours at 450° C. The calcined product was crushed to pass through a 850 micron sieve, blended with 2% by weight graphite and then pelleted to 3×3 mm equant pellets, with a force of 0.25 tons.

The final bath had the following composition and physical properties:

| Nickel content, % | 56.6 |
|---|---|
| Sodium content, % | undetected |
| Potassium content, % | undetected |
| Crush strength, kg | 8.8 |
| Bulk Density | 0.97 g/ml |
| Water loss | 11.2 |

As in the Example 2 the catalyst was subjected to the 270 hour sinter test but not at a sufficient temperature to remove all the volatile silicon species. Again the spectrum FIG. 6 shows a single peak in the range 900 cm$^{-1}$ to 1100 cm$^{-1}$ (at 1050 cm$^{-1}$) and the "labile silicon species" shoulder at around 1100 cm$^{-1}$. FIG. 7 shows a similar catalyst after hydrothermal treatment as described in Example 2 herein. As in the above examples the "labile silicon species" shoulder is again absent.

CATALYST ACTIVITY

Although the hydrothermal treatment causes considerable changes to the catalyst structure, as evidenced by its infra-red spectrum, the treated catalysts still retain catalytic activity for the methanation reaction. As a measure of catalytic activity, a sample of the catalyst, after reducing it in hydrogen to convert the nickel oxide to metallic nickel, is heated in a stoichiometric hydrogen and carbon monoxide mixture (3:1) at 20 bar, and the temperature at which the catalyst initiates the reaction recorded. Tests of this kind were carried out on the examples described above, after hydrothermal treatment. The results are given below:

| Example | Initiation Temperature °C. |
|---------|---------------------------|
| 1B | 208 |
| 2 | 252 |
| 3 | 200 |

It is clear that the treated catalysts retain a good activity for the methanation reaction:

We claim:

1. A process for the production of silicon containing methanation catalysts, comprising the steps of reducing a silicon-containing oxidic catalyst precursor at a temperature of at least 450° C. to produce a reduced catalyst, contacting the reduced catalyst with a gaseous mixture comprising steam and a reducing gas, reducing the temperature of the gaseous mixture while the same is in contact with the reduced catalyst and until liquid water condenses onto the catalyst, maintaining said catalyst in contact with said liquid condensed water for a period of time sufficient to cause silicon to be present in the catalyst in a non-labile form, and thereafter reheating the catalyst in a non-oxidising atmosphere to evaporate water therefrom.

2. A process as claimed in claim 1, wherein the reduced catalyst is contacted with a mixture of hydrogen and steam in a molar ratio of 9 moles steam per mole of hydrogen.

3. A process as claimed in claim 1 or claim 2 wherein the reduced catalyst is cooled to a temperature of about 300° C. prior to contact with said gaseous mixture.

4. A process as claimed in claim 1 wherein following contact with said gaseous mixture the catalyst is cooled to between 300° C. and 220° C. at a pressure of about 25 bar.

5. A process as claimed in claim 1 wherein following the reheating step, the catalyst is passivated by cooling in a non-oxidising atmosphere and thereafter contacting the catalyst with a mildly oxidising atmosphere.

6. A process as claimed in claim 5 wherein the mildly oxidising atmosphere is a carbon-dioxide containing gas or a mixture of oxygen and nitrogen.

* * * * *